United States Patent [19]

Parekh et al.

[11] Patent Number: 4,758,632

[45] Date of Patent: Jul. 19, 1988

[54] SELF-CROSS-LINKABLE ACRYLIC POLYMER CONTAINING HYDROXYALKYL CARBAMATE GROUPS AND COATING COMPOSITIONS CONTAINING THE SAME

[75] Inventors: Girish G. Parekh, Fairfield; Werner J. Blank, Wilton; William Jacobs, III, Bridgeport, all of Conn.

[73] Assignee: American Cyanamid Company, Stamford, Conn.

[21] Appl. No.: 698,713

[22] Filed: Feb. 6, 1985

Related U.S. Application Data

[63] Continuation-in-part of Ser. No. 581,012, Feb. 17, 1984, abandoned, and a continuation-in-part of Ser. No. 581,013, Feb. 17, 1984, abandoned.

[51] Int. Cl.[4] .............................................. C08F 8/00
[52] U.S. Cl. ................................. 525/383; 204/180.2; 204/181.4; 525/327.3; 525/328.2; 526/301
[58] Field of Search ................. 528/45, 73; 525/327.3, 525/328.2, 380, 379, 381, 382, 383

[56] References Cited

U.S. PATENT DOCUMENTS

| 4,100,143 | 7/1978 | Wolf | 526/301 |
| 4,543,276 | 9/1985 | Parekh | 427/388.3 |

FOREIGN PATENT DOCUMENTS

| 723214 | 12/1965 | Canada | 526/301 |
| 26300 | 7/1974 | Japan | 527/301 |

OTHER PUBLICATIONS

"Use of Urethane Glycols as Blocked Diisocyanates," Mikheev et al., Lakokras. Mater, Ikh Primen., 1983 (6), 5-6-abstract only from CA selects crosslinking Reactions, Issue 8, 1984.

*Primary Examiner*—Christopher Henderson
*Attorney, Agent, or Firm*—Roger S. Benjamin

[57] ABSTRACT

A self-cross-linkable acrylic polymer contains at least two hydroxyalkyl carbamate groups per molecule and may comprise the reaction product of an acrylic backbone polymer containing one or more suitable reactive groups and an amine containing one primary or secondary amine group and at least one hydroxyalkyl carbamate group or precursor thereof. Alternatively, the self-cross-linkable polymer may be obtained by polymerization of an acrylic polymerizable monomer containing at least one hydroxyalkyl carbamate group. The amine is joined to the monomer or backbone polymer by reaction of the primary or secondary amine group thereof with suitable reactive functional groups of the monomer or resin. A method of making the acrylic polymer, which is heat curable to provide a thermoset film or coating, comprises reacting the monomer or backbone polymer with an amine containing hydroxyalkyl carbamate groups or precursors thereof comprising hydrolyzable blocked primary amine groups. When present, the blocked groups are unblocked and reacted with a cyclic carbonate to form the hydroxyalkyl carbamate groups.

3 Claims, No Drawings

4,758,632

SELF-CROSS-LINKABLE ACRYLIC POLYMER CONTAINING HYDROXYALKYL CARBAMATE GROUPS AND COATING COMPOSITIONS CONTAINING THE SAME

This application is a continuation-in-part of U.S. Ser. Nos. 581,012 and 581,013, filed Feb. 17, 1984 both abandoned.

BACKGROUND OF THE INVENTION

The present invention concerns novel self-cross linkable acrylic resins containing hydroxyalkyl carbamate groups and coating compositions containing the same.

The reaction of propylene carbonate with primary and secondary amines to produce corresponding 2-hydroxypropyl carbamates is known in the art (Comp. rend, 1142, 1954). Similar reactions of ethylene carbonate are exemplified by the article, "The Preparation of Polymeric and Cyclic Urethans and Ureas from Ethylene Carbonate and Amines" by Elizabeth Dyer and Harvey Scott, *J.A.C.S.* (1956) pp. 672–675. See also the report "Polyurethane elastomers obtained without the use of diisocyanates" by L. Ya. Rappoport, G. N. Petrov, I. I. Trostyanskaya and O. P. Gavrilova in *International Polymer Science and Technology*, 8, No. 1, 1981. The Dyer-Scott reference discloses that polyurethanes might be prepared from 2-(hydroxyethyl)-carbamate by elimination of ethylene glycol, thereby avoiding the need for using diisocyanates. The Rappoport et al paper discloses generally the reaction of cyclic carbonates with amines to form polyurethane elastomers. Thus, the prior art shows an awareness that amines react with, e.g., propylene carbonate, to yield the corresponding hydroxyalkyl carbamates. *The Journal of Polymer Science*, Vol. 7, 899 916 (1969), in an article entitled "*New Method for Preparing Saturated and Unsaturated Aliphatic Polyurethanes*" by Y. Mizake, S. Ozaki and Y. Hirata, at pages 899–915, discloses alternate routes to saturated and unsaturated polyurethanes, including polycondensation reaction of glycol bis(chloroformate) with diamine.

An article by Richard D. Cowell entitled "Thermoplastic Polyurethane Elastomers: Chemistry Properties and Processing for the 80's" in the *Journal of Elastomers and Plastics*, Vol. 14, (October, 1982) pages 195–203, discloses the preparation of bis(2-hydroxyethyl) carbamates by reaction of diamines with ethylene carbonate followed by a catalyzed transesterification reaction with a glycol or macroglycol.

SUMMARY OF THE INVENTION

The present invention concerns acrylic polymers which contain at least two hydroxyalkyl carbamate groups per molecule and acrylic monomers which contain at least one hydroxyalkyl carbamate group and which are polymerized to form the acrylic polymers. The acrylic polymers of the present invention are self-cross-linkable through their hydroxyalkyl carbamate groups when heated at an elevated temperature and preferably in the presence of a suitable cross-linking catalyst. The monomers and polymers are obtained by reacting a suitable functional group of the acrylic monomer or acrylic backbone polymer which is reactive with a primary and/or secondary amine, i.e., by reacting an amine-reactive group of the acrylic monomer or acrylic backbone polymer with an hydroxyalkyl carbamate-containing amine or precursor thereof. Preparation of an hydroxyalkyl carbamate-containing secondary amine relies on the fact that multi-functional amines containing at least one primary and one hindered secondary amine group are, unexpectedly, selectively reactive with cyclic carbonates at the primary amine groups, leaving a secondary amine group unreacted in the resulting hydroxyalkyl carbamate-containing amine. The preparation of such hydroxyalkyl carbamate-containing amines is disclosed in copending application Ser. No. 581,006 filed Feb. 17, 1984 in the names of G. G. Parekh et al, the disclosure of which is incorporated by reference herein. The resultant hydroxyalkyl carbamate-containing amine has an unreacted secondary amine group which may be reacted with any suitable acrylic monomer or acrylic backbone resin which contains an amine-reactive functionality to provide acrylic monomers or polymers, the latter being self-cross-linkable through hydroxyalkyl carbamate groups.

In accordance with the present invention, there is provided a self-cross-linkable acrylic polymer which contains at least two hydroxyalkyl carbamate groups per molecule. Alternatively, the present invention relates to an acrylic polymerizable monomer containing at least one hydroxyalkyl carbamate group, such monomers being homopolymerizable or copolymerizable with suitable ethylenically unsaturated comonomers to yield the aforementioned self-cross-linkable acrylic polymers. In one aspect of the invention, the polymer is obtained as the reaction product of an acrylic resin containing one or more suitable amine-reactive sites and an amine having one primary or secondary amine group and at least one hydroxyalkyl carbamate group or precursor thereof, per molecule. In another aspect of the invention, the amine has one secondary amine group. The acrylic resin, prior to reacting with the hydroxyalkyl carbamate-containing amine may have an epoxy content of from about 0.5 to about 7 milliequivalents ("meq") epoxy per gram of resin solids. The amine-reactive groups are preferably one or more of anhydrides, N-methylolamides, pendant epoxies, isocyanates and N-methylol carbamates. In certain aspects of the invention, the amine-reactive sites of the acrylic polymer are epoxy functional groups, e.g., glycidyl ether moieties of the acrylic resin. As used herein and in the claims, an "acrylic polymer" means a polymer containing at least one acrylic moiety, and a "suitable" amine-reactive group is one which is reactive with the primary or secondary amine group of the polymer.

In one aspect of the invention, the polymer, which preferably has a molecular weight of from about 1,000 to about 50,000, is obtained by reaction of one or more acrylic resins having secondary amine-reactive, e.g., epoxy, groups with hydroxyalkyl carbamate-containing amines having one secondary amine group per molecule. Preferred hydroxyalkyl carbamate-containing amines are obtained as the reaction product of a cyclic carbonate, e.g., ethylene or propylene carbonate, with, e.g., diethylenetriamine or 4-amine-2,2,6,6-tetramethylpiperidine.

In one aspect of the invention, the polymer contains not more than about 0.1% by weight (solids basis) acid. IN another aspect of the invention, the polymer has from about 0.5 to about 10 meq hydroxyalkyl carbamate, preferably hydroxyethyl or hydroxypropyl carbamate, groups per gram of polymers solids. The hydroxyalkyl carbamate groups may be present as pendant and/or terminal groups.

Another aspect of the invention provides for a method of preparing the polymer of the invention by reacting an acrylic resin having one or more secondary amine-reactive groups thereon with an amine containing one secondary amine group and at least one group selected from the class consisting of hydrolyzable blocked primary amine groups and hydroxyalkyl carbamate groups and, when said blocked primary amine groups are present, hydrolyzing the same to unblock the primary amine groups and then reacting a cyclic carbonate with the primary amine groups to form hydroxyalkyl carbamate groups. Alternatively, the polymer may be prepared from the corresponding monomers, by homo- or copolymerization as herein described above, wherein the monomers either before or after polymerization contain hydrolyzable blocked primary amine groups which are deblocked by hydrolysis and reacted with primary amine groups to form hydroxyalkyl carbamate groups.

Generally, the acrylic urethan polymers of the invention are heat curable without release of formaldehyde during cure, the leaving groups during cure being low-toxicity diols. The resulting self-cross-linkable acrylic-urethane polymers are useful in coatings, adhesives, laminating resins and textile and paper finishes.

In one aspect of the invention, there is provided a coating composition comprising a liquid medium containing a self-cross-linkable acrylic polymer as described above.

In other aspects of the invention, the coating composition includes a cross-linking catalyst, preferably a metal-containing cross-linking catalyst, more preferably a tin-containing cross-linking catalyst, such as dibutyltin-dilaurate, or one selected from the group consisting of quaternary ammonium, phosphonium and arsonium compounds and ternary sulfonium compounds. The catalyst is preferably present in the amount of from about 0.1 to about 10% by weight, preferably from about 1 to about 5% by weight, of polymer solids. In a preferred aspect, low cure temperatures are faciliated by using polymers of low acid content, for example, polymers containing not more than about 0.1% by weight acid.

Another aspect of the invention includes applying a composition comprising the polymer of the invention and a suitable cross-linking catalyst onto a substrate and heating the coated substrate at a temperature and for a time sufficient to cure the applied composition. For example, in the presence of a suitable cross-linking catalyst the applied composition is curable at relatively low temperatures, e.g., from about 200 to about 250° F. (from about 93 to about 121° C.) and within about one hour, e.g, about 20 to about 30 minutes.

Another aspect of the invention provides for utilizing acrylic monomers or polymers as described in the following detailed description, including those having functional groups as described below, to prepare monomers and polymers containing groups as described at (a) through (e) of the following detailed description.

Other aspects of the invention include utilizing backbone resins and amines of the general and specific formulas indicated below to form the polymers of the invention including polymers comprising repeating units and modifying units as described in the following detailed description.

The polymers of the present invention are well suited to be applied to a substrate by any suitable means, including electrodeposition or application by roller, spray or dipping, or by powder coating techniques.

DETAILED DESCRIPTION OF THE PREFERRED EMBODIMENTS

Generally, hydroxyalkyl carbamate-containing amines may be reacted with suitable acrylic monomers or acrylic backbone resins which contain sites which are reactive with primary or secondary amines (or both) to provide the monomers and polymers of the present invention. The hydroxyalkyl carbamate-containing amines may be made by reacting one or more amines and cyclic carbonates to yield compounds having the formula:

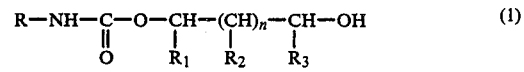

wherein R is an organic moiety having at least one unreacted secondary amine group, each of $R_1$, $R_2$ and $R_3$ is independently H or a $C_1$ to $C_{20}$ alkyl, cycloalkyl or alkyl aromatic moiety or any such moiety containing one or more heteroatoms, and n is 0 or 1. Such moieties containing one or more heteroatoms include, for example, those containing ether groups, thio groups and organo-silicon moieties.

The cyclic carbonate to be reacted with the multifunctional amine may comprise any suitable cyclic carbonate, including biscarbonates, which is reactive with one or more of the primary amine groups of a multifunctional amine. Generally, five-member ring organic carbonates are preferred as compared to six-member ring organic carbonates, the latter being relatively more expensive and difficult to prepare. Accordingly, a preferred cyclic carbonate utilizable in the present invention has the formula:

wherein $R_a$ and $R_b$ may be the same or different, and each maya comprise H, or a $C_1$ to $C_8$ aliphatic, cycloaliphatic, aromatic or heterocyclic groups. Ethylene carbonate (dioxolane-2-one), both $R_a$ and $R_b$=H, and propylene carbonate (4-methyldioxolane-2-one), $R_a$=H and $R_b$=$CH_3$, are preferred reactants.

The multi-functional amine utilized in the invention contains a secondary amine group which is hindered with respect to reacting with the cyclic carbonate and at least one primary amine group. As used herein and in the claims, (a) "multi-functional amine" means an amine containing at least one primary and at least one hindered secondary amine group; and (b) "hindered secondary amine group" means a secondary amine group which is inhibited, sterically, electronically or otherwise, with respect to reacting with the cyclic carbonate under conditions at which the primary group will react. It has been discovered that, surprisingly, the well known reactivity of primary and secondary amines with cyclic carbonates is highly selective to the primary group for certain multi-functional amines. Stated otherwise, it has been found that certain multi-functional amines have secondary amine groups which are sterically or otherwise inhibited from reacting with a cyclic carbonate, and yet are reactive with, for example, epoxy groups or other functional groups available on backbone polymers. Thus, hindered secondary amine groups contained in multi-functional amines utilizable in accordance with the present invention enable the formation, with one or more cyclic carbonates, of hydroxyalkyl carbamates in which secondary amine groups remain unreacted and available to react with epoxy or other active groups. This enables the anchoring of hydroxyalkyl carbamate groups on the acrylic monomer or acrylic resin by reaction of the secondary amine groups with secondary amine-reactive groups on the acrylic monomer or backbone polymers. For example, when ethylene and propylene carbonates were reacted with diethylenetriamine, they reacted selectively with the primary amine groups of the triamine to form carbamate groups while leaving the secondary amine groups unreacted. Such secondary amine groups can then be reacted with, for example, epoxy groups on acrylic monomers or polymers, without affecting the carbamate groups. The resultant hydroxyalkyl carbamate-containing acrylic polymers of the invention can self-cross-link to yield thermoset acrylic resins suitable for a number of applications, for example, in the area of coatings. The self-cross-linking reaction may be base catalyzed or tin-catalyzed, which offers significant advantages over prior amino resin systems which require acid catalyzation. Thus, the present invention enables the utilization of a system which is free of formaldehyde and in which cure inhibition in the presence of hindered amine ultraviolet stabilizers is avoided.

In order to provide a site on the monomer or backbone resin on which the amines may be anchored, each molecule of such monomer or backbone resin should have at least one, and preferably more, reactive sites thereon which can react with the secondary amine group of the hydroxyalkyl carbamate-containing amine of the invention. Such reactive sites may include, without limitation, one or more of the following groups.

(Acid halides, in which X is a halogen, preferably Cl, Br or I)

(Halogenated Aliphatics, in which X is a halogen, preferably Cl, Br or I)

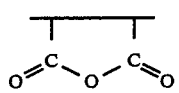
(Anhydrides)

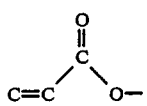
(alpha, beta unsaturated esters)

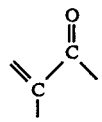
(alpha, beta unsaturated ketones)

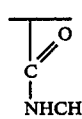
(N—Methylolamides)

-continued

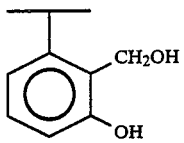
(Methylolated Phenols)

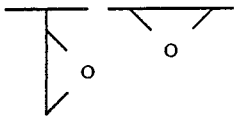
(Epoxies)

—NCO (Isocyanates)

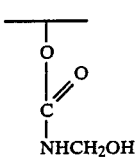
(N—Methylol Carbamates)

—SO$_2$X
(in which X is a halogen preferably Cl, Br or I)

Reaction of the secondary aine group of the hydroxyalkyl carbamate-containing amine with acrylic polymers containing functional groups as illustrated above, will result in the formation of the following groups at the functional group sites.

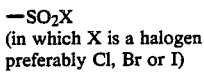

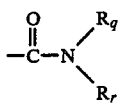

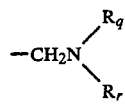

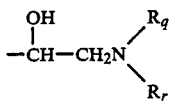

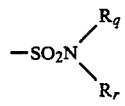

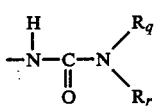

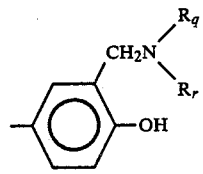

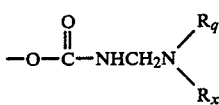

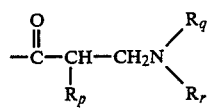

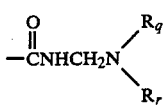

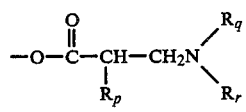

wherein $R_p$ is H or $C_1$-$C_8$ alkyl; and $R_q$ and $R_r$ may be the same or different and are amine residues containing hydroxyalkyl carbamate moieties.

The repeating units of which the polymer is comprised may fall into two categories, one comprising units containing the suitable amine-reactive functional groups as described above and the other comprising modifying units selected to impart desired film-making or other properties to the polymer and the finished coating or other product made therefrom. Generally, any suitable repeating units may be employed in the polymer in any desired combination provided that there exist in the polymer sufficient suitable reactive functional groups for attachment thereto of the primary or secondary amines utilized in the reaction. The polymeric backbone structure may comprise amine-reactive repeating units derived from one or more of glycidyl methacrylate, glycidyl acrylate, isocyanatoethylmethacrylate, maleic anhydride, methacryloyl chloride, n-methylolacrylamide, 1-(1-isocyanato-1-methylethyl)-3-(1-methylethenyl)benzene, 1-(1-isocyanato-1-methylethyl)-4-(1-methylethenyl)benzene, methyl acrylamidoglycolate, methyl acrylamidoglycolate methyl ether, acryloyl chloride and chloromethyl styrene. The polymeric backbone structure may also include modifying units derived from one or more of acrylic acid, methacrylic acid, butadiene, styrene, alpha-methyl styrene, methyl methacrylate, butyl acrylate, acrylonitrile, hydroxyethyl acrylate, glycidyl methacrylate, acrylamide, methacrylamide, vinyl chloride and vinylidene chloride.

The use of the hydroxyalkyl carbamate-containing amines to prepare the compound of the present invention may be illustrated as follows. The hydroxyalkyl carbamate-containing compounds may be reacted with any suitable acrylic monomer or backbone polymer containing, for example, epoxy groups, in which case the reaction may be represented as

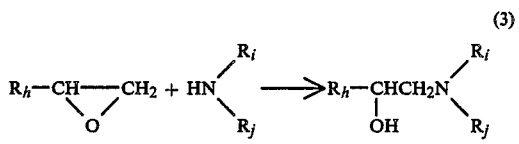
(3)

where $R_h$ is a fragment of an epoxy-containing acrylic monomer or resin and $R_i$ and $R_j$ are fragments of the hydroxyalkyl carbamate-containing amine or polyamine compounds of the invention. The reaction usually occurs at room or slightly elevated temperatures and is often exothermic. The reaction may be performed without a solvent, otherwise aprotic or alcohol solvents may be used. Any of numerous types of acrylic monomers of backbone polymers having any of a variety of reaction functional groups thereon may also be used, as described in more detail below. For example, a typical polymer having anchored thereon one or more of the compositions of the invention may have the formula

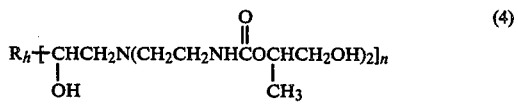
(4)

The resultant polymer, upon heating and, optionally, in the presence of a suitable cross-linking catalyst, will cross-link through one or more mechanisms, as follows: by cross-linking through backbone hydroxyl groups, e.g.

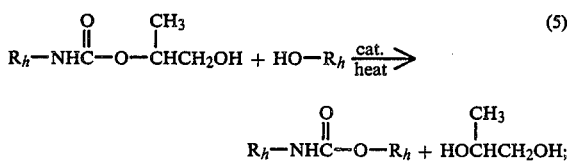
(5)

by cross-linking through self-condensation, e.g.

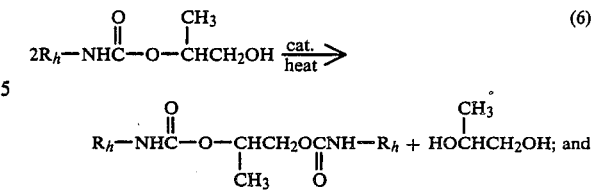
(6)

by cross-linking through backbone amine groups, e.g.,

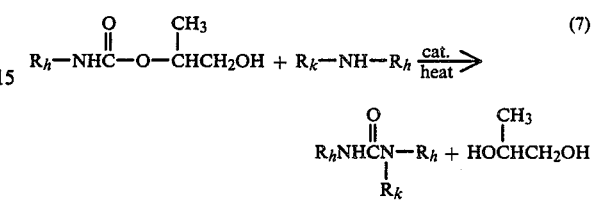
(7)

wherein $R_k$ is hydrogen or a fragment of the backbone acrylic polymer.

As indicated above, the acrylic polymers of the invention can be prepared by reacting either acrylic backbone polymers or acrylic monomers containing suitable functional groups with primary or secondary amines containing one or more hydroxyalkyl carbamate groups or precursors thereof. When acrylic monomers are thus employed, they are polymerized, after reaction with the amines, either by homopolymerization or copolymerization with other monomers, to provide the acrylic polymers of the invention. As used herein, "suitable" functional groups simply means those functional groups, such as epoxy, isocyanato, methylol, etc., which are reactive with the primary or secondary amine groups of the hydroxyalkyl carbamate-containing amines. For example, an hydroxyalkyl carbamate-containing monomer may be prepared by reacting glycidyl methacrylate with an hydroxyalkyl carbamate-containing secondary amine. The resulting monomer may then be homo- or co-polymerized to provide an acrylic polymer of the invention.

The repeating units of which the polymer is comprised may fall into two categories, one comprising units containing the suitable amine-reactive functional groups and the other comprising modifying units selected to impart desired film-making or other properties to the polymer and the finished coating or other product made therefrom. Any suitable repeating units may be employed in the polymer in any desired combination provided that there exist in the polymer sufficient suitable reactive functional groups for attachment thereto of the primary or secondary amines utilized in the reaction.

In an alternate method of preparing the acrylic polymer of the invention, the acrylic monomer or backbone resins are reacted with amines which contain, in addition to a primary or secondary amine group, hydrolyzable, blocked primary amine groups, e.g., ketimine groups in lieu of some or all of the hydroxyalkyl carbamate groups. After reaction of the primary or secondary amine groups with, e.g., the epoxy groups as described above, so that the amine groups are pendant upon the monomer or backbone resin, the ketimine groups are hydrolyzed to form free primary amine groups and one or more suitable cyclic carbonates are then added to the mixture to react with the resultant free amine groups. Thus, the multi-functional amine utilized to form the hydroxyalkyl carbamate-containing amine will contain either amine groups reactable with a cyclic carbonate or groups such as ketimine groups convertible to an amine group reactable with the cyclic carbonate.

The Multi-Functional Amines

A wide range of multi-functional amines are utilizable in the present invention to react with the cyclic carbonate inasmuch as, as stated above, it is necessary only that the multi-functional amine contain at least one primary and one hindered secondary amine. For example, one class of multi-functional amines utilizable in the present invention may be represented by the formula:

$$R_c-(NH-R_d)_{n2}-NH-R_e$$

wherein $n_2$ is 0 to 5, and each $R_c$, $R_d$ and $R_e$ is independently a straight chain or branched hydrocarbon fragment having 2 to 6 carbon atoms each and at least one of $R_c$ and $R_e$ contains a primary amine group.

The formulas of suitable classes of amines may be derived simply by replacing with $-NH_2$ the hydroxyalkyl carbamate moieties of the compounds set out in formulas (8) to (11) below.

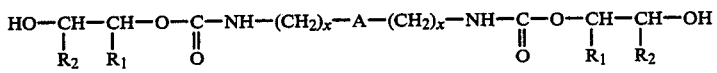
(8)

where A is $[NH\,(CH_2)_x]_n NH$, n is 0 to 10, each x is independently 2 to 6, preferably 2; each of $R_1$ and $R_2$ is independently H, or a $C_1$ to $C_{20}$ alkyl or alkyl aromatic moiety, preferably, H or $CH_3$. Preferably, n is not more than 10, more preferably, is from 0 to 6, most preferably from 0 to 4. Compositions in which x is 2 or 6 may readily be made from widely available reactants, i.e., diethylenetriamine and dihexamethylenetriamine and to that extent are preferred.

Another suitable class of compounds is represented by the formula:

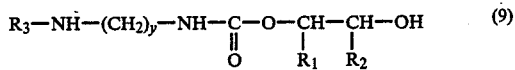
(9)

wherein y is 2 or 3, each of $R_1$ and $R_2$ is as defined above, and $R_3$ is a $C_1$ to $C_{20}$ alkyl, cycloalkyl or alkyl aromatic moiety or any such moiety containing, in addition to at least one carbon atom, one or more heteroatoms. In this class of compounds, starting materials which would provide alkyl, cycloalkyl or alkyl aromatic moieties greater than $C_{20}$ are not readily available. The $C_1$ to $C_{20}$ alkyl, cycloalkyl or alkyl aromatic moieties of all the formulas given herein, and somewhat shorter chains, i.e., $C_1$ to $C_{18}$ alkyl, cycloalkyl or alkyl aromatic moieties, are to that extent are preferred.

Another class of suitable compounds is represented by the formula:

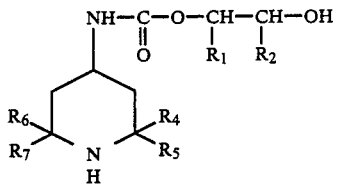
(10)

wherein each of $R_1$ and $R_2$ is as defined above, each of $R_4$ and $R_6$ is independently H or a $C_1$ to $C_4$ alkyl moiety and each of $R_5$ and $R_7$ is independently a $C_1$ to $C_4$ alkyl moiety. Preferably, $R_1$ and $R_2$ are independently H or $CH_3$ and each of $R_4$, $R_5$, $R_6$ and $R_7$ is $CH_3$.

Another suitable class of compounds in accordance with the invention has the formula:

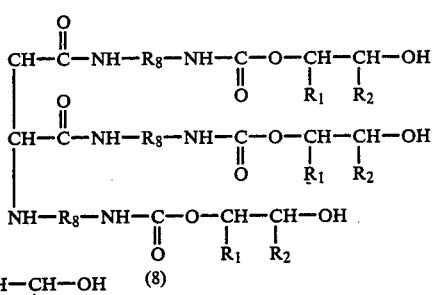
(11)

wherein each of $R_1$ and $R_2$ is as defined above and each $R_8$ is independently a $C_2$ to $C_6$ alkylene moiety, preferably $-(CH_2)_2-$ or $-(CH_2)_6-$.

A wide variety of acrylic monomers and acrylic backbone resins containing amine-reactive sites may be employed to react with the hydroxyalkyl carbamate-containing amines to provide the monomers and polymers of the invention, depending on the characteristics desired for the finished coating or other product. The secondary amine-reactive groups of the acrylic monomer or resin provide sites on the monomer or backbone resin on which the amines may be anchored. The hydroxyalkyl carbamate-containing resin should contain not more than one secondary amine group per molecule inasmuch as the presence of more than one such secondary amine group per molecule will cause gellation.

Any suitable acrylic resin may be utilized as the backbone resin in accordance with the present invention. Any one of a variety of one or more monomers may be utilized to prepare an acrylic resin, and at least one of the monomers being polymerized to form the backbone resin contains at least one secondary amine-reactive group if the hydroxyalkyl carbamate groups are added by reaction of the hydroxyalkyl carbamate-containing amine with the polymer after its formation. Alternatively, such monomers may prior to their polymerization be reacted with the hydroxyalkyl carbamate-containing amine to form polymerizable acrylic monomers containing at least one hydroxyalkyl carbamate group. Suitable monomers for polymerization or pre-polymerization reaction with hydroxyalkyl carbamate-containing amines include, by way of illustration and not limitation, alkyl acrylates such as butyl acrylate, butyl methacrylate, ethyl acrylate, 2-ethyl hexyl acrylate, hydroxyethyl acrylate, hydroxyethyl methacrylate, acrylamide, methyl methacrylate, acrylonitrile, glycidyl methacrylate, glycidyl acrylate, vinyl acetate, styrene, substituted styrenes, alphamethyl styrene, etc. Generally, a preferred class of acrylic monomers and resins are those containing pendant glycidyl ether groups.

The acrylic monomers described hereinabove may suitably be copolymerized with other compatible ethylenically unsaturated monomers to form the polymers of the present invention. Potentially suitable monomers include, by way of example and not limitation, maleic anhydride, methacryloyl chloride, n-methyloylacrylamide, 1-(1-isocyanato-1-methylethyl)-3-(1-methylethenyl)benzene, 1-(1-isocyanato-1-methylethyl)-4-(1-methylethenyl)benzene, methyl acrylamidoglycolate, methyl acrylamidoglycolate methyl ether, acryloyl chloride and chloromethyl styrene.

If the polymer of the invention is formed as an acrylic backbone resin containing amine-reactive sites, the acrylic resin preferably has an active site content prior to reaction with the secondary amine containing hydroxyalkyl carbamate groups (or precursors thereof, as explained below) of from 0.5 to 7 milliequivalents ("meq") per gram of the acrylic polymer. The backbone resin and monomers may also have other functional sites, such as hydroxy and amide groups. It is preferred that the polymer of the invention have as low an acid content as possible in order to facilitate low temperature cure of the polymer containing hydroxyalkyl, e.g., hydroxypropyl and/or hydroxyethyl, carbamate groups. The monomers from which the acrylic resin is prepared are sometimes contaminated with acids, such as methacrylic or propionic acids, in amounts of, e.g, 0.3 to 1% by weight. It is preferred that the acid content of the polymer of the invention be not more than about 0.1% by weight of the polymer in order to attain relatively low temperature cures. The acrylic polymer itself may also have 0.5 to 10 meq per gram of pendant or terminal hydroxyalkyl, e.g., hydroxypropyl and/or hydroxyethyl, carbamate groups.

The Acrylic Monomers and Thermosettable Acrylic Polymers of the Invention

The acrylic monomers and polymers of the invention can be modified by reacting them with selected organic secondary amines (in addition to the hydroxyalkyl carbamate-containing amines) such as diethylamine, dibutylamine, morpholine, n-methylaniline, and the like. The selection and combination of specific modifying secondary amines of course depends on the end use of the polymer. For example, in the preparation of water-reducible polymers one or more hydrophilic secondary amines may be reacted with some of the functional sites on the backbone resin in order to enhance hydrophilicity of the polymer. Conversely, for applications where hydrophobicity of the polymer is desired, for example, for electrodepositable coatings, it may be necessary or desirable to react one or more hydrophobic secondary amines with the backbone resin to impart the desired degree of hydrophobicity to the polymer. Generally, the polymers of the invention are well suited for utilization in the field of coatings and in such case preferably have molecular weights in the range of from about 1,000 to about 50,000, more preferably in the range of from about 2,000 to about 20,000. The urethane crosslinkable polymers of the invention are particularly well suited for a variety of uses in the field of coatings, such as solvent or water based coatings, powder coatings, electrocoating compositions, spray roller and dip type coatings, and the like. Such coatings are normally applied to a substrate such as a metal, textile, plastic or paper. The thermosetting resins of the invention may be used to prepare urethane coatings which are resistant to organic solvents and water and are abrasion-resistant, as well as adhesives and laminating resins.

A coating formulation containing the acrylic polymers of the invention may be modified by incorporating into the formulation other additives such as amino formaldehyde resin, reactive diluents, etc. to change the physical, chemical and mechanical properties of the resulting coatings.

The acrylic polymers described in this invention are particularly useful as binders for conventional solvent based coatings, electrocoating, powder coating, etc., and may be formulated with or without a catalyst.

The preparation of the hydroxyalkyl carbamate-containing amines, which are to be reacted with suitable acrylic backbone resins to obtain the polymers of the invention, is illustrated by Examples 1-4, following.

EXAMPLE 1

To a 3-neck flask suitable equipped with a stirrer and a thermometer were added 103 grams (1 mole) of diethylenetriamine and 200 grams of methanol. To the resulting methanolic solution of diethylenetriamine was added 184.8 grams (2.1 moles) of ethylene carbonate in slow increments. At the completion of the ethylene carbonate addition the reaction temperature had risen from room temperature to 65° C. The reaction mixture was allowed to react for several hours without any external heat. After removal of methanol, the residue solidified on standing. The solid residue was recrystallized from ethanol. The recrystallized white solids were isolated in 90% yields. The product was characterized by I.R., N.M.R. and potentiometric titration to be bis(2-hydroxyethyl) (imminodiethylene)biscarbamate, m.p. 98° C.

EXAMPLE 2

To 168 grams (1.65 moles) of propylene carbonate was added 51 grams (0.5 mole) of diethylenetriamine in 150 ml. of methanol at 15° C. After complete addition the mixture was allowed to react for 24 hours to 25° C. Potentiometric titration indicated the presence of free secondary amine. The reaction mixture was heated to 70° C. for 3 hours. After this period there was very little change in the free amine content as indicated by titration. Methanol was removed from the mixture to obtain a syrupy liquid at about 72% solids containing bis(2-hydroxy-1-methylethyl) (imminodiethylene)biscarbamate. The analysis of the product by FAB mass spectroscopy also confirmed the composition to consist mainly of the above compound.

EXAMPLE 3

To a 3 neck flask suitably equipped with stirrer and a thermometer was added 62.4 grams (0.4 mole) of 4-amino-2,2,6,6-tetramethylpiperidine (ATP) and 150 grams methanol. To this solution was added 52.8 grams (0.6 mole) of ethylene carbonate and the mixture was heated to 70° C. for two hours. The separated white solids were filtered at 25° C. and washed with methanol to yield 63.5 grams (65% of theory) of a product of mp 190° to 192° C. I.R., N.M.R. and potentiometric titration confirmed the structure to be 2-hydroxyethyl(2,2,6,6-tetramethyl-4-piperidinyl)carbamate.

The following two examples illustrate the preparation of hydroxyalkyl carbamate-containing monomers, which are to be polymerized to form the hydroxyalkyl carbamate-containing polymers of the invention.

EXAMPLE 3A

To 24 grams of 1,2-dimethoxyethane were added 7.1 grams of glycidyl methacrylate and 13.7 grams of the hydroxyalkyl carbamate of Example 2. The reaction mixture was heated to 85° C. for four hours and 1,2-diemthoxyethane was removed by distillation under reduced pressure. The resulting water white product was viscous and glassy and contained 0.3 millimols per gram of free residual epoxy groups. The mass spectrum showed a major peak corresponding to the mass of the desired product of the following structure:

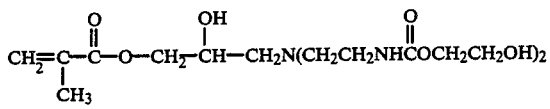

EXAMPLE 3B

To a suspension of 27.9 grams of the hydroxyalkyl carbamate of Example 2 in 100 grams of t-butanol was added 20.8 grams of 1-(1-isocyanato-1-methylethyl)-3-(1-methylethenyl)benzene. The reaction mixture was stirred with a high speed stirrer. Most of the solids dissolved after 2 hours and I.R. showed a small amount of unreacted isocyanate. The reaction mixture was stirred overnight, then filtered to remove trace amount of insolubles, and t-butanol was distilled from the filtrate under reduced pressure. The N.M.R. of the resulting product showed it to be of the following structure:

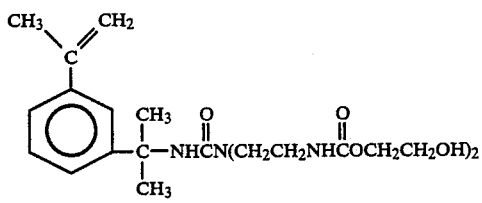

The following two examples illustrate polymerization of the hydroxyalkyl carbamate-containing monomers of Examples 3A and 3B to provide polymers in accordance with the invention.

EXAMPLE 3A-1

To a suitable 3 neck flask equipped with stirrer and a thermometer are added 50 grams of 2-ethoxyethanol. At reflux temperature, a blend of 60 grams of N-butylacrylate, 20 grams of styrene, 59 grams of the monomer of Example 3A, 1 gram of N-dodecyl mercaptan and 2 grams of dicumyl peroxide in 50 grams of 2-ethoxyethanol is added to the flask over a period of 2 hours. The reaction mixture is held at 145° C. for 2 hours. The resulting resin of 58% solids has a basic nitrogen content of 1 meq per gram of resin solids, and an hydroxyethyl carbamate content of 2 meq per gram of resin solids.

EXAMPLE 3B-1

To a suitable 3 neck flask equipped with a stirrer and a thermometer are added 175 grams of toluene. At reflux temperature a blend of monomers comprising 58.9 grams of N-butylacrylate, 45 grams of methyl methacrylate, and 71.2 grams of the hydroxypropyl carbamate-containing monomer of Example 3B is added to the toluene along with 4 grams of t-butylperbenzoate as the initiator. After 4 hours at reflux a resin containing hydroxypropyl carbamate group is obtained. The resin comprises 50% solids and contains 1.65 meq hydroxypropyl carbamate per gram of resin solids.

EXAMPLE 4

To a 3-neck flask suitably equipped with stirrer and a thermometer was added 62.4 grams (0.4 mole) of ATP (see Example 3) and 25 grams of methanol, followed by 61.2 grams (0.6 mole) of propylene carbonate. The reaction mixture was heated and allowed to reflux for five hours. On standing overnight at 25° C., white crystalline solids had separated. The crystalline solids were filtered and washed with a small amount of methanol to yield 82 grams (79.4% theoretical) of a product of m.p. 135° C. The N.M.R. analysis indicated the product to be a mixture of isomeric hydroxypropyl carbamates containing primary and secondary hydroxy groups in 2:1 mole ratios.

A catalyst may be used as part of a formulation to promote cross-linking of the polymer of the invention. The catalyst may be external catalyst or it may be incorporated as an internal catalyst during preparation of the backbone polymer, as is known in the art. For example, quaternary ammonium hydroxide groups may be incorporated into the backbone resin. While any suitable cross-linking catalyst may be utilized (such as known tin, zinc, and titanium compounds) ternary or quaternary compounds as described below are preferred. Benzyltrimethyl ammonium hydroxide, dibutyltindilaurate, and similar compounds are good catalysts for achieving cross-linking at elevated temperatures in the range of 100° to 175° C. (212° to 347° F.) for a period of a few seconds to about 30 minutes. A catalyst may be present in a formulation in the amount of from 0.1 to 10% by weight of the polymer, preferably, 1 to 5% by weight of the polymer.

Preferably, the catalyst may comprise ternary or quaternary catalysts such as known compounds of the formula:

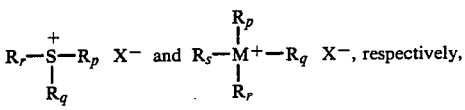

where $R_p$, $R_q$, $R_r$ and $R_s$ may be equivalent or different and may be a $C_1$ to $C_{20}$ aliphatic, aromatic, benzylic or cyclic aliphatic moiety and the like, where M may be nitrogen, phosphorus or arsenic (to provide, respectively, quaternary ammonium, phosphonium or arsonium compounds), where S is sulfur (to provide a ternary sulfonium compound) and where $X^-$ may be hydroxide, alkoxide, bicarbonate, carbonate, formate, acetate, lactate, and other carboxylates derived from volatile organic carboxylic acids or the like. Such salts of carboxylic acids are effective to promote the low temperature cure provided that the carboxylic acid portions of the salt are volatile.

In preparing coating compositions in accordance with the invention, which are water soluble or dispersible, the hydrophilic polymer is dissolved or dispersed in an aqueous medium which optionally may contain a suitable organic cosolvent and, when an external catalyst is utilized, a catalyst such as dibutyltindilaurate or a quaternary ammonium compound is added. Generally, the external quaternary or ternary catalysts are selected so that they are water soluble or dispersible. Strong bases such as alkali metal hydroxides (KOH, NaOH, LiOH, etc.) may also be included as catalysts in the composition.

The following examples illustrate the preparation and utilization of specific compositions in accordance with the present invention.

Examples 5-6 illustrate the preparation of acrylic-urethane compositions in accordance with the present invention. Example 7 is a comparative formulation having pendant hydroxyethyl groups but no hydroxyalkyl carbamate groups.

EXAMPLE 5

A. An acrylic polymer containing glycidyl ether groups is prepared as follows. 100 grams 2-ethoxyethanol was added to a 3-neck flask suitably equipped with stirrer, a thermometer, and a condenser and heated to 135° C. Over a two hour period, a blend of 60 grams of n-butyl acrylate, 20 grams of styrene, 20 grams of glycidyl methacrylate, 2 grams of dicumyl peroxide, and 1 gram of n-dodecyl mercaptan was added to the heated 2-ethoxyethanol. After the complete addition of the monomer blend containing an initiator and a chain transfer agent, the reaction temperature was held at 140° C. for two hours. Throughout the polymerization reaction a nitrogen blanket was maintained in the reactor. The resultant resin had solids content of 47% and epoxy content of 0.64 meq per gram.

B. To the acrylic resin obtained in part A of this Example was added 36 grams (0.13 mole) of bishydroxyethyl carbamate derivative of diethylenetriamine (the hydroxyalkyl carbamate of Example 1) and the mixture was heated to 80° C. for two hours and then to 120° C. for two hours. The resulting resin had the following characteristics. Solids: 56.5%, Viscosity: U-V, Gardner Color: 5-6, Basic Nitrogen Content: 0.51 meq per gram and Epoxy Content: less than 0.05 meq per gram.

EXAMPLE 6

The procedure of Example 5 was repeated except that instead of the carbamate of Example 1, 30.2 grams of the hydroxypropyl carbamate of ATP of Example 4 was reacted with 93.75 grams of the acrylic resin of Part A of Example 5 (on solids basis). The reaction was carried out in the presence of 53 grams of 2-ethoxyethanol at 145° C. for 18 hours. The resultant acrylic polymer had the following characteristics. Solids: 70%, Basic Nitrogen Conent: 0.69 meq per gram, and Epoxy Contents: 0.1 meq per gram.

EXAMPLE 7 (COMPARATIVE EXAMPLE)

In a 3-neck flask suitably equipped with a stirrer, a thermometer, and a condenser 33 grams of 2-ethoxyethanol was heated to 135° C. To this was added slowly over a two hour period a blend of 60 grams of n-butyl acrylate, 20 grams styrene, 20 grams of 2-hydroxyethylmethacrylate of very low acid content, 1 gram of dicumyl peroxide, and 1 gram of n-dodecyl mercaptan. After complete addition of the monomer blend containing the initiator and the chain transfer agent, the reaction temperature was held at 140° C. for two hours. Throughout the polymerization reaction a nitrogen blanket was maintained in the reactor. The resultant resin had the following characteristics:

Solids: 75%, Acid number: 0.4, and Hydroxy number: 85 (on solids basis).

COATING FORMULATIONS

Four clear coating formulations were prepared by blending the polymer of Example 5 with various catalysts as shown in Table I. These coating formulations were cast on zinc phosphate pretreated cold rolled steel panels and cured at elevated temperatures. The cure conditions and film properties are shown in Table II. The results in Table II show that the polymer of Example 5 self-cross-links at temperatures as low as 125° C. in 20 minutes. Tin catalyzed cross-linked acrylic-urethane films show good humidity and salt spray resistance. All the self-cross linked films show excellent resistance to methyl ethyl ketone double rubs. Use of a hydrophobic quaternary catalyst such as methyltricaprylyl ammonium hydroxide results in self-cross-linked films which are better in humidity and salt spray resistance than those obtained from the formulation containing a hydrophilic quaternary benzyltrimethyl ammonium hydroxide.

TABLE I

| Formulation: | Parts by Weight | | | |
| Contents | I | II | III | IV |
| --- | --- | --- | --- | --- |
| The Polymer of Example 5 | 10 | 10 | 16 | 23 |
| Dibutyltindilaurate | 0.1 | — | — | — |
| Benzyltrimethylammonium hydroxide (40% in methanol) | — | 0.2 | — | — |
| Tetrabutyldiacetoxy stannoxane | — | — | 0.2 | — |
| Methyltricaprylylammonium hydroxide (72%) | — | — | — | 0.7 |

TABLE II

| Formulation | I | I | II | II |
| --- | --- | --- | --- | --- |
| Cure Schedule | 175° C. 20 min. | 150° C. 20 min. | 122° C. 20 min. | 150° C. 20 min. |
| Film Thickness (micro-meters) | 31 | 25 | 25 | 28 |
| Knoop Hardness | 13.7 | 6.6 | 7.4 | 7.1 |
| Pencil Hardness | H-2H | F-H | H-2H | H-2H |
| Impact (Reverse in. lbs.) | 30-40 | 60 | 80 | 80 |
| MEK Rub Resistance | 100+ | 100+ | 100+ | 100+ |
| Humidity Resistance (65° C.) | 21 days | 21 days | 2-3 hours | 2-3 hours |
| Salt Spray Resistance | 200 hours | 200 hours | Less than 8 hrs | Less than 8 hrs |

| Formulation | III | III | IV | IV |
| --- | --- | --- | --- | --- |
| Cure Schedule | 122° C. 60 min. | 150° C. 20 min. | 125° C. 20 min. | 150° C. 20 min. |
| Film Thickness (micro-meters) | 22 | 22 | 38 | 33 |
| Knoop Hardness | 3.9 | 7.3 | 7.1 | 8.3 |
| Pencil Hardness | F-H | H-2H | F-H | F-H |
| Impact (Reverse in. lbs.) | 60 | 60 | 30-40 | 20-30 |
| MEK Rub Resistance | 100+ | 100+ | 100+ | 100+ |
| Humidity Resistance (65° C.) | — | — | 24 hours | 3 days |
| Salt Spray Resistance | — | — | 60 hours no corrosion. Loss of adhesion at | 60 hours no corrosion. Loss of adhesion at |

TABLE II-continued

|  | scribe | scribe |
| --- | --- | --- |

EXAMPLE 8

A. A clear electrocoating system was prepared by emulsification of 70 grams of the polymer of Example 5 with deionized water in the presence of 1 gram of dibutyltindilaurate catalyst and 1.1 grams of acetic acid, to 10% solids. The pH and conductivity of the 10% solids electrocoating emulsion were 4.8 abd 175 microm-ho$^{-1}$cm$^{-1}$ respectively. Zince phosphate pretreated cold rolled steel panels were electrocoated at 100 volts for 30 seconds and later rinsed with deionized water. The electrocoated panels were cured at 150° C. and 175° C., respectively, for 20 minutes. The resulting films had good organic solvent resistance and good hardness as shown below.

| Film Properties of Electrocoated Films of this Example | | |
| --- | --- | --- |
| Cure Schedule | 150° C., 20 min. | 175° C., 20 min. |
| Film Thickness (micro-meters) | 17.5 | 22.5 |
| Knoop Hardness | 5.8 | 9.3 |
| MEK Rubs | 200+ | 200+ |
| Impact (Rev) in-lbs. | 40 | 30–40 |
| Salt Spray Resistance (120 hrs.) | 8.5 mm | 8.3 mm |

The following Example 9 illustrates a clear coating obtained by use of a polymer of the invention.

EXAMPLE 9

Cast films obtained from the polymer of Example 6, catalyzed with 1% tetrabutyldiacetoxy stannoxane, were cured at 150° C. for 20 minutes. The cured films had good MEK rub resistance, however, the films were soft. The polymer of Example 6 can potentially be also useful as a hindered amine light stabilizer for thermoset and thermoplastic materials.

The following Example 10 illustrates a pigmented coating obtained by use of a polymer of the invention.

EXAMPLE 10

74.4 grams of the polymer of Example 5, 1.5 grams of benzyltrimethylammonium hydroxide (40% in methanol), and 30 grams of OR ® 650 rutile titanium dioxide pigment were dispersed in a sand mill. The filtered white enamel was cast on zinc phosphate pretreated cold rolled steel panels by a wirecater. The coated panels were cured at elevated temperatures to yield hard, flexible, and organic solvent resistant, white glossy coatings. Cure schedule and film properties are shown below.

|  | I | II |
| --- | --- | --- |
| Cure Schedule, 20 min. | 122° C. | 150° C. |
| Film Thickness (micro-meters) | 37 | 30 |
| Knoop Hardness | 3.1 | 9.3 |
| Pencil Hardness | F-H | H-2H |
| Impact (Reverse) | 60 in-lbs | 60 in-lbs |
| MEK Rubs | 100+ | 100+ |

EXAMPLE 11 (COMPARATIVE EXAMPLE)

A. Three formulations were prepared using, respectively, the polymers of Examples 5 and 7 in combination with 2-ethyl hexanol blocked toluene diisocyanate (TDI-EHA) prepared according to U.S. Pat. No. 3,984,299, and benzyl trimethyl ammonium hydroxide (BTMA) as the catalyst.

| Formulation | I | II | III |
| --- | --- | --- | --- |
| Polymer of Example 5 | 12.3 | — | — |
| Polymer of Example 7 | — | 23.3 | 20.0 |
| TDI—EHA | 3.2 | 7.9 | 10.2 |
| BTMA (40%) | 0.25 | 0.6 | 0.6 |

The films were cast on zinc phosphate pretreated cold rolled steel and cured at 125° C. for 20 minutes. Films obtained from formulation I, containing the polymer of Example 5 and having pendant hydroxyethyl carbamate groups had good MEK rub resistance, indicating that film was cross-linked. Formulations II and III containing the polymer of Example 7, having pendant hydroxyethyl ester groups had no MEK to rub resistance, indicating that films were not cross-linked. This shows that hydroxyethyl carbamate behaves chemically differently from hydroxyethyl esters.

B. Three formulations as shown below were prepared using the polymer of Example 7, in combination with BTMA, dibutyltindilaurate (DBTL) and tetrabutyldiacetoxy stannoxane (TDS) as catalysts. The films were cast on zinc phosphate pretreated cold rolled steel and baked at 150° C. for 20 minutes. None of the films had good MEK rub resistance after the bake, indicating poor cross-linking. The polymer of Example 5 under similar conditions gave well cross-linked films (See Table II above, under the heading "COATING FORMULATIONS").

| Formulation | I | II | III |
| --- | --- | --- | --- |
| Polymer of Example 7 | 10 | 10 | 10 |
| BTMA (40%) | 0.2 | — | — |
| DBTL | — | 0.2 | — |
| TDS | — | — | 0.2 |

EXAMPLE 12

A. To a reactor suitably equipped and under a nitrogen blanket was added 131 grams of anhydrous toluene. To this a blend of 59 grams of n-butylacrylate, 45 grams of methylmethacrylate and 30.1 grams of 1-(1-isocyanato-1-methylethyl)-3-(1-methylethenyl)benzene was added at 105° C. followed by 2.1 grams of t-butylperbenzoate initiator. The reaction temperature was maintained at 105° C. for 3 hours. An additional 2 grams of the initiator was added and the reaction temperature was raised to 116° C. and this temperature maintained for 5 hours. The resulting polymer had 50% solids and an NCO content of 2.5% by weight.

B. In a suitable reactor under a nitrogen blanket was added 44.5 grams of isocyanate group containing polymer of part A of this Example, followed by addition of 10 grams of an 80% solution of bis(2-hydroxy-1-methylethyl) (iminodiethylene)biscarbamate in isobutanol, and 10 grams of isobutanol at ambient temperature. There was a slight exotherm initially; the reaction mixture was held at 30° C. for 2 hours. After this period I.R. of the reaction mixture showed absence of the isocyanate band and presence of the band for substituted urea. Titration of the resulting product showed no free amine.

Coating Formulations

The polymer of Example 12 was formulated into a clear coating formulation using dibutyltindilaurate (DBTL), tetrabutyldiacetoxy stannoxane, (TDS), and benzyltrimethylammonium hydroxide (BTMA), catalysts as shown below.

| Formulation | I | II | III |
|---|---|---|---|
| Polymer of Example 12 | 10 | 10 | 10 |
| DBTL | 0.1 | — | — |
| TDS | — | 0.1 | — |
| BTMA (40%) | — | — | 0.2 |

The cure schedule and film properties of the above formulations are shown below.

| Formulation | I | II | III |
|---|---|---|---|
| Cure Schedule: | 150° C. (20 min.) | 150° C. (20 min.) | 125° C. (20 min.) |
| Film Thickness (micro-meters): | 18 | 15 | 22 |
| Pencil Hardness: | 3H–4H | 3H–4H | H–2H |
| Impact (reverse) in/lbs: | 20–30 | 20–30 | 5–10 |
| MEK Rub Resistance: | 100+ | 100+ | 100+ |

Although the foregoing examples are directed to the reaction of acrylic resins with secondary amines containing hydroxyalkyl carbamate or precursor groups, primary amines containing such carbamate or precursor groups may also be employed, as previously stated. However, it will be recognized by those skilled in the art that primary amines can act as difunctional reactive sites so that gellation of the reaction mixture may occur with certain classes of amine-reactive functional groups such as, for example, epoxides, allylic or benzylic halides, or functional groups which involve Mannich or Michaels type reactions. Therefore, secondary amines are a preferred class of reactants. However, one of ordinary skill in the art can readily determine by the simple expedient of a conventional gellation test whether a specific composition of reactants will be suitable for the desired application.

Generally, reference herein and in the claims to hydroxyalkyl carbamates and compounds containing the same, including structural formulas of the same, is intended to include the various isomeric species thereof, if any.

While the invention has been described in detail with respect to specific preferred embodiments, it will be apparent to one skilled in the art that numerous variations may be made to the embodiments without departing from the spirit and scope of the invention.

What is claimed is:

1. A method of preparing a self-cross-linkable acrylic polymer having at least two hydroxyalkyl carbamate groups per molecule comprises reacting (a) an acrylic resin having at least one suitable amine-reactive group thereon with (b) an amine containing one primary or one secondary amine group and at least one group selected from the class consisting of hydrolyzable blocked primary amine groups and hydroxyalkyl carbamate groups and, when said blocked primary amine-groups are present, hydrolyzing the same to unblock said primary amine groups and then reacting a cyclic carbonate with said primary amine groups to form said hydroxyalkyl carbamate groups.

2. The method of claim 1 wherein the amine (b) contains one secondary amine group.

3. The method of claim 1 wherein said amine-reactive group comprises glycidyl ether groups.

* * * * *